United States Patent

Lehto et al.

[11] Patent Number: 5,818,586
[45] Date of Patent: Oct. 6, 1998

[54] MINIATURIZED FABRY-PEROT SPECTROMETER FOR OPTICAL ANALYSIS

[75] Inventors: Ari Lehto, Helsinki; Stefan Lindblad; Altti Torkkeli, both of Espoo; Martti Blomberg, Vantaa, all of Finland

[73] Assignees: Valtion Teknillinen Tutkimuskeskus, Espoo; Vaisala Oy, Helsinki, both of Finland

[21] Appl. No.: 550,804

[22] Filed: Oct. 31, 1995

[30] Foreign Application Priority Data

Oct. 31, 1994 [FI] Finland ................. 945124

[51] Int. Cl.$^6$ .................... G01B 9/02
[52] U.S. Cl. ............. 356/346; 356/352
[58] Field of Search ............. 356/346, 352; 385/12, 14

[56] References Cited

U.S. PATENT DOCUMENTS 4,859,060  8/1989  Katagiri et al. ........... 356/352
5,247,186  9/1993  Toda .

FOREIGN PATENT DOCUMENTS 0-331338  9/1989  European Pat. Off. .
0-367675  5/1990  European Pat. Off. .
0-608049  7/1994  European Pat. Off. .
91806     4/1994  Finland .

*Primary Examiner*—Samuel A. Turner

[57] ABSTRACT

A miniaturized spectrometer for gas concentration measurement includes a radiation source for admitting electromagnetic radiation onto the gas to be measured, a detector for detecting the radiation transmitted through or emitted from the gas, an electrically tunable Fabry-Perot interferometer placed in the path of the radiation prior to the detector, control electronics circuitry for controlling the radiation source, the interferometer and the detector. The radiation source, the detector, the interferometer and the control electronics are integrated in a miniaturized fashion onto a common, planar substrate and the radiation source is an electrically modulatable micromechanically manufactured thermal radiation emitter.

26 Claims, 3 Drawing Sheets

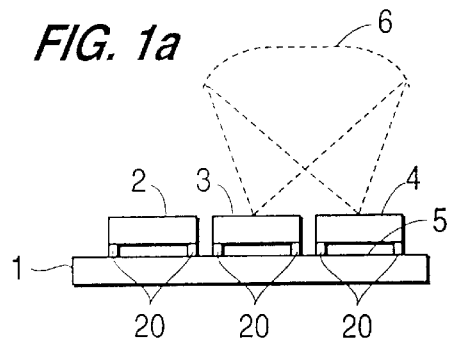
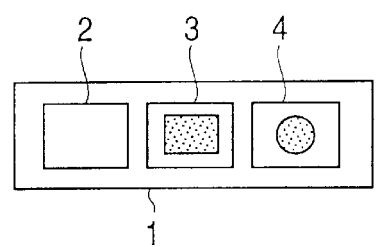
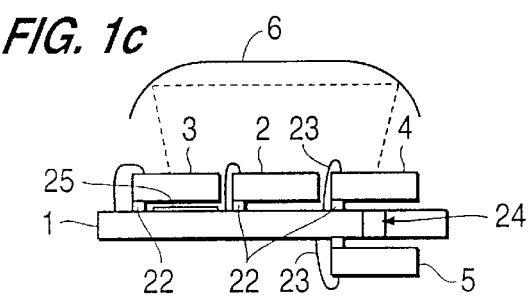
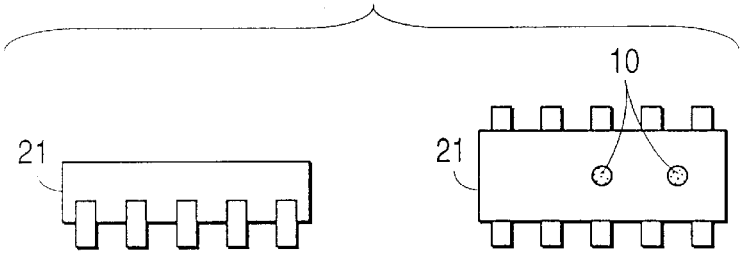
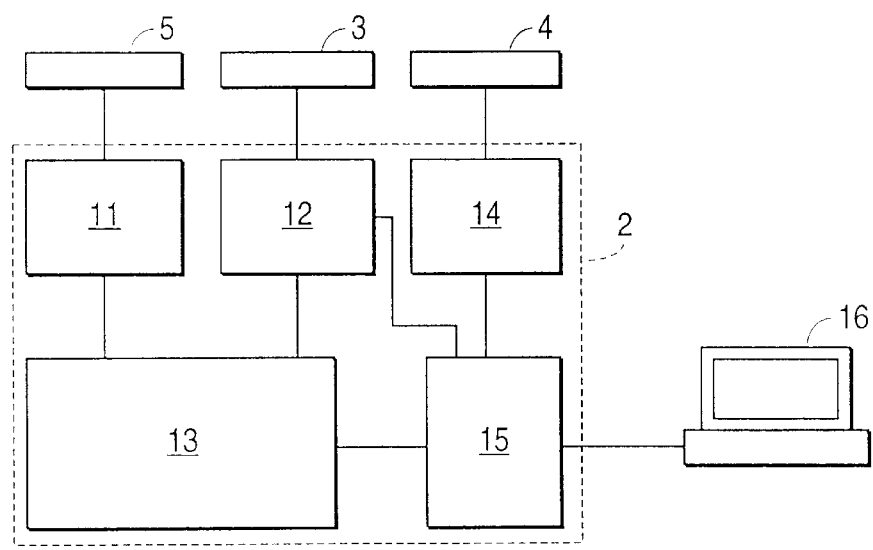

MINIATURIZED FABRY-PEROT SPECTROMETER FOR OPTICAL ANALYSIS

FIELD OF THE INVENTION

The present invention relates to a spectrometer including a radiation source, a detector and a Fabry-Perot interferometer.

The invention is intended for use in the analysis of optical emission or absorption spectra in the visible and IR range.

DESCRIPTION OF RELATED ART

Nondispersive optical spectrum analyzers conventionally use different types of optical filters. An important category of these filter are bandpass filters, typically tuned to a fixed wavelength. If measurement is desired to be carried out on two wavelengths, two filters are required with a change-over mechanism to change the filter position in an appropriate manner, or alternatively, a separate detector is placed behind each filter. The filter change operation is conventionally implemented by means of a rotating disk to which the filters are attached. During the rotation of the disk, the detector output signal is obtained as an AC voltage (or current) which is a more advantageous form of the measurement output signal than a DC signal.

A problem of the rotating disk mechanism is its relatively short service life due to wear of the bearings. Also the size of the rotating motor and the disk makes real system miniaturization impossible. An advantageous embodiment would be a filter construction in which the bandpass center wavelength could be electrically tuned without the need for any movable parts involving wear in continuous use.

Electrostatically tunable, silicon-based interferometers fabricated by micromechanical techniques are known from publications 1, 8 and 2. The construction disclosed in cited publications 1 and 8 is comprised by a bulk component made by micromechanical techniques from two or three silicon wafers. Such a construction requires auxiliary electrostatic deflection electrodes for the parallelism control of the interferometer mirrors.

Cited publication 2 discloses a surface micromechanical, electrostatically tunable interferometer array for use in the visible light range. The size of the individual interferometers in the array is as small as $20 \times 20 \, \mu m^2$. Interferometers of this small size can be used only in conjunction with single-mode optical fibers.

The IR source according to conventional techniques typically is a temperature-stabilized, massive bulk component with no means of intensity modulation.

Known manufacturing techniques of microelectronics and micromechanics also offer a facility of manufacturing miniature-size, electrically modulatable radiation sources from silicon 3, 4, 5. The structure of these components is formed by polysilicon thin films with a typical thickness of approx. 1 $\mu m$ and a length of hundreds of $\mu m$. Their width may vary from a few $\mu m$ to tens of $\mu m$. The thermal capacity of such a silicon glow filament is so low that a modulation frequency of hundreds of Hz can be used.

Infrared detectors manufactured using silicon micromechanical techniques are known from, e.g., publications 6 and 7.

SUMMARY OF THE INVENTION

It is an object of the present invention to overcome the drawbacks of the above-described techniques and to provide an entirely novel type of miniaturized, integrated spectrometer.

The goal of the invention is achieved by integrating all components including radiation source, detector and control electronics on a single, planar substrate.

More specifically, the spectrometer according to the invention integrates the radiation sources, the detector, the interferometer and the control electronics. Further, the radiation source is electrically modulatable.

The invention offers significant benefits.

All subunits of the spectrometer can be mass-produced, whereby an advantageous cost structure of the components is attained. Further, encapsulation of the spectrometer in a standard package offers cost benefits. The spectrometer can be mounted on a printed-circuit board thus facilitating the manufacture of a miniature-size analyzer incorporating a processor. The spectrometer functions are comprehensively user-programmable. Particularly for carbon dioxide concentration measurement applications the spectrometer can be manufactured so cost-effectively as to make its use as, e.g., the sensor element of a ventilation system economically viable.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention will be examined in more detail by means of exemplifying embodiments with reference to the attached drawings, in which:

FIG. 1a is a side view of a first embodiment of the integrated spectrometer according to the invention;

FIG. 1b is a top view of the embodiment of the integrated spectrometer according to the invention;

FIG. 1c is a side view of another embodiment of the integrated spectrometer according to the invention;

FIG. 2 is a side and top view of a packaged embodiment of the spectrometer according to the invention;

FIG. 3 is a block diagram of the functions of the integrated spectrometer according to the invention;

FIG. 5b is a sectional side view of the radiation source illustrated in FIG. 5a;

FIG. 7b is a cross-sectional side view of the structure illustrated in FIG. 7a.

DETAILED DESCRIPTION OF THE PREFERRED EMBODIMENTS

Figure 4A:
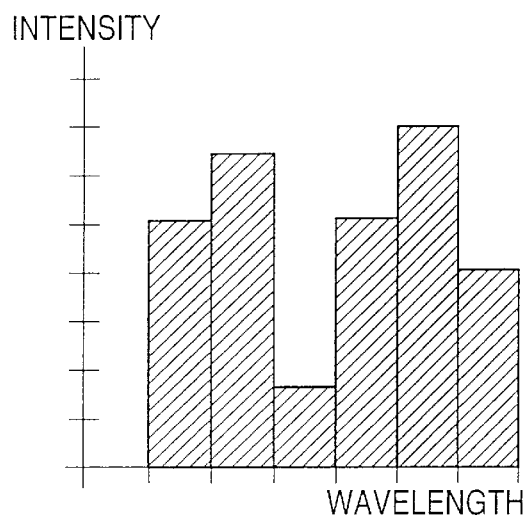
FIG. 4a is a graph showing the intensity transmission curve of a spectrometer embodiment according to the invention plotted as intensity vs. wavelength.

A spectrometer can be employed in the analysis of emission or absorption spectra. Absorption measurements require the use of the spectrometer's own radiation source, while emission measurements can be performed without activating the source.

Referring to FIG. 1, a miniaturized spectrometer according to the invention is shown in a longitudinally sectional view. Here, onto a silicon substrate 1 is integrated a radiation-sensitive detector 5. Further, an electronics microcircuit 2, a radiation source 3 and a Fabry-Perot interferometer 4 are integrated on the silicon substrate 1. An external mirror 6 brings the incoming radiation into focus on the interferometer. The IR radiation source 3, the detector 5 as well as the interferometer 4 are implemented in silicon micromechanics. The mutual order of these sections 2, 3 and 4 may be varied. Black balls 20 depict solder globules used in the flip-chip bonding technique.

Referring to FIG. 1c, alumina may also be used as the substrate material. In this embodiment the detector 5 is placed on the opposite side of the substrate relative to the interferometer, and the radiation path is formed by an opening 24 made to the substrate. The radiation source 3 and the detector are placed at the extreme opposite ends of the component to provide maximum length of the optical path. Also, the mirror 6 can-be made larger in the embodiment. Optionally, a dual-part mirror can be used. As an alternative bonding technique is herein shown the gluing 22 of the components at one corner only to avoid problems associated with thermal expansion. Another method of overcoming this problem is to use a resilient adhesive. The electrical contacts are made by wire bonding 23. The radiation source 3 can be provided with a reflecting surface 25 to maximize the optical output power and to prevent the heating of the substrate 1. The surface 25 may be an evaporated gold layer, or alternatively, a multilayer silicon mirror.

Referring to FIG. 2, the spectrometer can be encapsulated in, e.g., a DIL (Dual-in-Line) package 2. The cover of the package can be provided with openings 10 for unobstructed passage of radiation.

Referring to FIG. 3, the microcircuit 2 incorporates all electronic functions required by the analyzer. A preamplifier 11 of the detector performs front-end amplification of the measurement signal obtained from the detector 5. The control of the radiation source 3 is accomplished by means of a controller 12 incorporating a D/A converter, an oscillator and a driver stage. A phase-locked amplifier 13 is employed to synchronize the detection process with the control of the radiation source 3. The interferometer driver section 14 incorporates a D/A converter and an amplifier. The function of the driver section 14 is to control the center wavelength of the passband of the interferometer 4. An input/output port 15 makes it possible to connect the spectrometer to an external microcomputer 16. The microcomputer 16 can thus control the spectrometer as well as control/set the oscillator frequency of the IR radiation source 3 and the sweep mode of the interferometer 4. The microcomputer 16 also performs data collection from the output signal of the phase-locked amplifier 13.

Figure 4B:
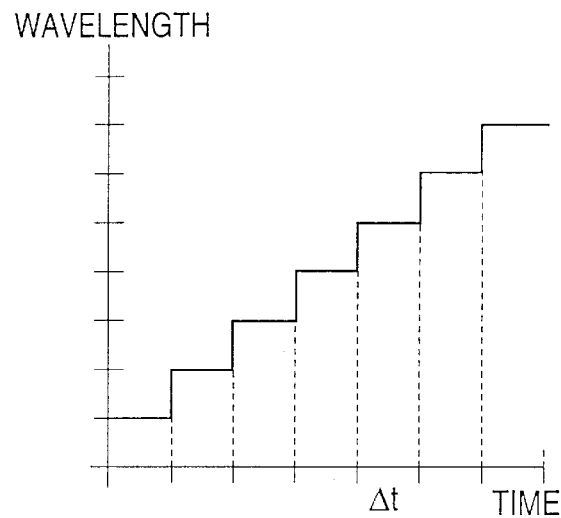
FIG. 4b is a graph showing the passband center wavelength control of a spectrometer embodiment according to the invention as a function of time.

Referring to FIG. 4a, a typical spectrum measured using the interferometer is shown. The function of the interferometer is further elucidated in FIG. 4b. The center wavelength of the interferometer passband is stepped in a desired manner by applying an appropriate control to the driver section 14 of the interferometer 4. By stabilizing the passband to a desired wavelength for the duration of an appropriate time $\Delta t$, data collection can be performed from the output signal of the phase-locked amplifier 13. The duration $\Delta t$ of each measurement step can be varied according to the intensity of the impinging radiation, that is, a longer data collection time can be allocated for measuring a wavelength component with a weaker intensity. Further processing of the raw data can be performed with the help of the microcomputer 16.

Besides those depicted, the microcircuit may provide alternative functions. Hence, the above-given description should be understood as not limiting the function of the invention.

Figure 5A:
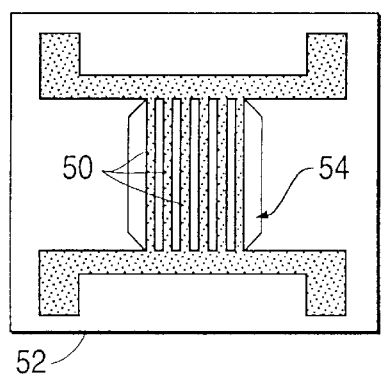
FIG. 5a is a top view of an embodiment of the radiation source employed in the spectrometer according to the invention.
Figure 5B:
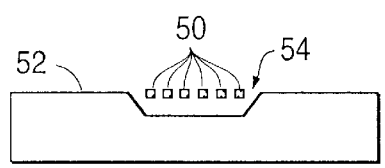

The IR radiation source of the spectrometer is formed by a micromachined glow filament, or a microlamp, having a basic structure illustrated in FIG. 5.

The emitting elements are formed by electrically in parallel connected glow filaments 50 comprising silicon nitride coated thin-film polysilicon or tungsten wires. The substrate material 52 is monocrystalline silicon into which is etched a well 54 under the glow filaments 50 for the purpose of reducing heat dissipation losses. The emitting surface area is typically about a square millimeter. When desired, also the radiation source may be integrated into the substrate in the same fashion as the detector.

Figure 6:
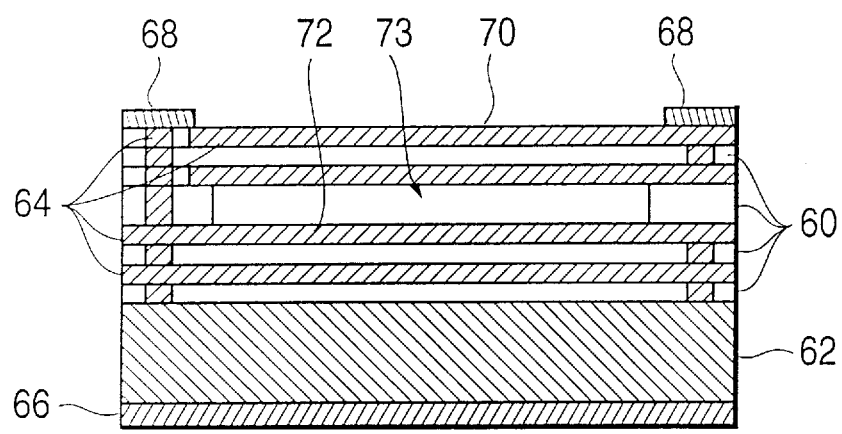
FIG. 6 is a longitudinally sectional side view of a Fabry-Perot interferometer embodiment used in the spectrometer according to the invention.

The interferometer section is formed by a silicon micromechanically manufactured, electrically tunable, optical Fabry-Perot resonator. The basic structure of the interferometer is shown in FIG. 6. The resonator length is controlled by means of an electrical field applied between the resonator mirrors.

Deposited on a monocrystalline silicon substrate 62, the interferometer comprises a multilayer structure in which the three uppermost layers form a first mirror 70. The second mirror 72 comprises the four lowermost layers deposited onto the substrate 62. A nitride layer 66 formed on the underside of the substrate 62 serves as an anti-reflection layer. The optical resonator is formed in the center part of the cavity 73 between the mirrors 70 and 72. The area of the optical cross section is about a square millimeter. Flip-chip bonding is made to metallized areas 68. In the diagram, the similarly oblique-hatched areas 64 are polysilicon and the white areas 60, respectively, (with the exception of the cavity 73) are silicon oxide.

Figure 7A:
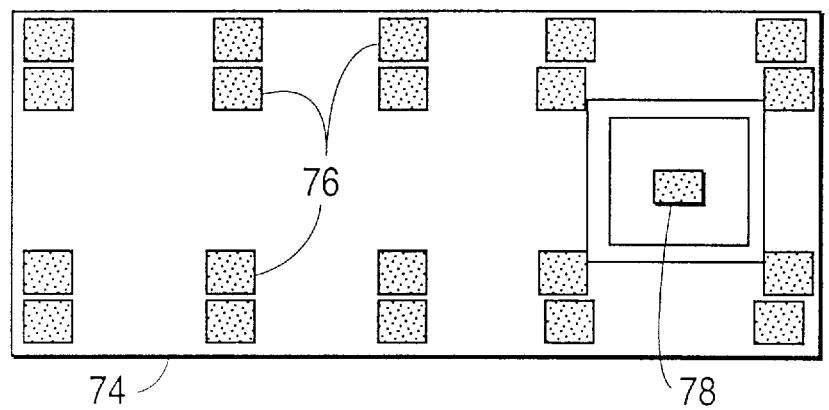
FIG. 7a is a top view of the IR detector in the structure according to the invention.
Figure 7B:
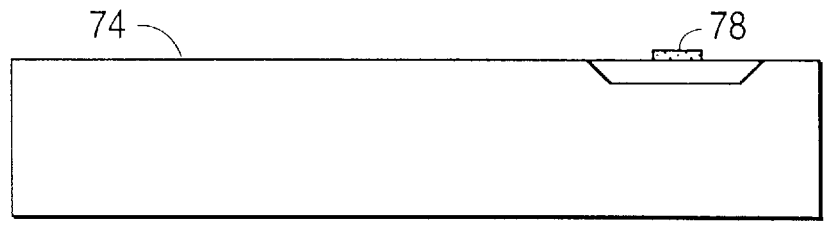

The substrate comprises a square silicon chip having the IR detector 78 integrated on it. The basic structure of the substrate is shown in FIG. 7. The substrate size is approx. 5×13 mm².

Squares 76 marked with black are the flip-chip bonding and wire connection areas.

The substrate has additional, not shown thin-film conducting patterns. Substrate silicon has been removed from under the detector 78. The detector 78 may be a thermopile or bolometer detector in the IR range and a silicon photodiode in the visible wavelength range.

Also the interferometer 4 and/or the control electronics circuitry 2 may be integrated onto the substrate 1.

The embodiment according to the invention is particularly suited for the measurement of carbon dioxide concentrations. Other advantageous applications could be found in the measurement of industrial process gases with a high concentration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

1 J. H. Herman and D. J. Clift, "Miniature Fabry-Perot Interferometers Micromachined in Silicon for use in Optical Fiber WDM Systems", Digest of Technical Papers, Transducers '91, 372, San Francisco 1991.

2 K. Aratani et al., "Surface Micromachined Tuneable Interferometer Array", Digest of Technical Papers, Transducers '93, 678, Yokohama 1993.

3 H. Guckel and D. W. Burns, "Integrated transducers based on black-body radiation from heated polysilicon films", Transducers '85, 364–6 (Jun. 11–14, 1985).

4 Carlos H. Mastrangelo, James Hsi-Jen Yeh, and Richard S. Muller: "Electrical and optical characteristics of vacuum sealed polysilicon microlamps", *IEEE Transactions on Electron Devices,* 39, 6, 1363–75 (June 1992).

5 M. Parameswaran, A. M. Robinson, D. L. Blackburn, M. Gaitan and J. Geist, "Micromachined thermal radiation emitter from a commercial CMOS process"; *IEEE Electron Device Lett.,* 12, 2, 57–59 (1991).

6 G. R. Lahiji and K D. Wise, "A Batch-Fabricated Silicon Thermopile Infrared Detector". *IEEE Transactions on Electron Devices.* ED-29, I (January 1982).

7 I. H. Choi and K. D. Wise. "A Silicon-Thermopile-Based Infrared Sensing Array for Use in Automated Manufacturing", *IEEE Transactions on Electron Devices,* ED-33, 1 (January 1986).

8 N. F. Railey and D. R. Ciarlo and J. C. Koo and B. Beiriger and J. Trujillo and C. Yu and G. Loomis and R. Chow. "A Fabry-Perot Microinterferometer for Visible Wavelengths." In Fifth IEEE Solid-State Sensor and Actuator Workshop, editors, Stephen D. Senturia. pages 170–173, Hilton Head Island, S.C., June 22–25, 1992.

We claim:

1. A spectrometer for optical measurement, said spectrometer comprising:

an infrared radiation source for admitting electromagnetic radiation;

a thermionic detector for detecting radiation from the optical measurement;

an electrically tunable Fabry-Perot interferometer placed in the path of the radiation prior to the detector; and control electronics circuitry for controlling the radiation source, the interferometer and the detector, wherein the detector, the interferometer and at least one of the radiation source and the control electronics are integrated in a miniaturized fashion onto a common, planar substrate, the detector and the interferometer being spaced apart from one another on the common planar substrate.

2. The spectrometer as defined in claim 1, wherein the infrared radiation source is integrated onto the common, planar substrate and further comprising an external mirror for directing radiation from the optical measurement onto the detector.

3. The spectrometer as defined in claim 1, wherein the control electronics circuitry includes a preamplifier of the detector for amplifying the signal of the detector, a drive of the radiation source, a phase-locked amplifier, a driver of the interferometer and an input/output port suited for interconnecting the spectrometer with an external computer (16).

4. The spectrometer as defined in claim 1, wherein the radiation source is integrated onto the substrate.

5. The spectrometer as defined in claim 1, wherein the control electronics circuitry is integrated onto the substrate.

6. The spectrometer as defined in claim 1, wherein the detector is a thermopile.

7. The spectrometer as defined in claim 1, wherein the detector is a bolometer.

8. The spectrometer as defined in claim 1, wherein the control electronics, the radiation source and the interferometer are bonded onto the substrate using flip-chip techniques.

9. The spectrometer as defined in claim 1, wherein the spectrometer is encapsulated in a DIL package.

10. The spectrometer as defined in claim 9, wherein the package is provided with openings in order to provide unobstructed passage of the measured radiation.

11. The spectrometer as defined in claim 1, wherein the radiation source is an electrically modulatable micromechanically manufactured thermal radiation emitter.

12. The spectrometer as defined in claim 1, wherein the detector and the interferometer are on opposite sides of the common, planar substrate.

13. A method for optical measuring comprising:

integrating a detector, an electrically tunable Fabry-Perot interferometer and at least one of a radiation source and control electronics in a miniaturized fashion onto a common, planar substrate;

emitting electromagnetic radiation, via the radiation source, for the optical measuring;

detecting, via the detector, at least one of the radiation from the optical measuring;

placing the interferometer in the path of the radiation prior to the detector, said placing including spacing the interferometer and the detector apart from one another on the substrate; and controlling, via the control electronics circuitry, the radiation source, the interferometer and the detector.

14. The method as defined in claim 13, further comprising placing an external mirror in the immediate vicinity of the spectrometer.

15. The method as defined in claim 13, wherein said integrating step includes bonding the control electronics, the radiation source and the interferometer onto the substrate using flip-chip techniques.

16. The method as defined in claim 13, further comprising encapsulating the spectrometer in a DIL package.

17. The method as defined in claim 16, further comprising providing the package with openings in order to provide unobstructed passage of the measured radiation.

18. The method as defined in claim 13, wherein said spacing includes positioning the interferometer on the common, planar substrate on a side opposite the detector.

19. A spectrometer for optical measurement, said spectrometer comprising:

a radiation source for admitting electromagnetic radiation for the optical measurement;

a detector for detecting radiation from the optical measurement;

an external mirror for directing radiation from the optical measurement onto the detector;

an electrically tunable Fabry-Perot interferometer placed in the path of the radiation prior to the detector; and control electronics circuitry for controlling the radiation source, the interferometer and the detector, wherein the radiation source and at least one of the detector and the interferometer are integrated onto a common, planar substrate.

20. The spectrometer as defined in claim 19, wherein the control electronics circuitry includes a preamplifier of the detector for amplifying the signal of the detector, a drive of the radiation source, a phase-locked amplifier, a driver of the interferometer and an input/output port suited for interconnecting the spectrometer with an external computer.

21. The spectrometer as defined in claim 19, wherein the detector is integrated onto the substrate.

22. The spectrometer as defined in claim 19, wherein the interferometer is integrated onto the substrate.

23. The spectrometer as defined in claim 19, wherein the control electronics circuitry is integrated onto the substrate.

24. The spectrometer as defined in claim 19, wherein the detector as a thermionic detector.

25. The spectrometer as defined in claim 19, wherein the detector is a photodiode.

26. A method for optical measuring comprising:

integrating a radiation source and at least one of a detector and an electrically tunable Fabry-Perot interferometer in a miniaturized fashion onto a common, planar substrate;

emitting electromagnetic radiation, via the radiation source, for the optical measuring;

detecting, via the detector, at least one of the radiation transmitted through and emitted from the gas;

directing radiation form the optical measurement onto the detector;

placing the interferometer in the path of the radiation prior to the detector; and controlling, via the control electronics circuitry, the radiation source, the interferometer and the detector.

* * * * *